United States Patent
Falciano et al.

(10) Patent No.: US 12,370,735 B2
(45) Date of Patent: Jul. 29, 2025

(54) METHOD FOR USE IN MEASURING A PROPERTY OF AN AUTOMOBILE COMPONENT

(71) Applicant: C.R.F. SOCIETÀ CONSORTILE PER AZIONI, Turin (IT)

(72) Inventors: Marika Falciano, Turin (IT); Paolo Chiappero, Turin (IT); Graziano Brocani, Turin (IT); Fabio Scaffidi Muta, Turin (IT); Valentina Brunella, Turin (IT)

(73) Assignee: C.R.F. Società Consortile per Azioni, Orbassano (IT)

( * ) Notice: Subject to any disclaimer, the term of this patent is extended or adjusted under 35 U.S.C. 154(b) by 711 days.

(21) Appl. No.: 17/595,743

(22) PCT Filed: Aug. 10, 2020

(86) PCT No.: PCT/IB2020/057508
§ 371 (c)(1),
(2) Date: Nov. 23, 2021

(87) PCT Pub. No.: WO2021/116784
PCT Pub. Date: Jun. 17, 2021

(65) Prior Publication Data
US 2022/0314519 A1    Oct. 6, 2022

(30) Foreign Application Priority Data
Dec. 10, 2019  (EP) .................................. 19214709

(51) Int. Cl.
*B29C 48/92* (2019.01)
*B29C 48/00* (2019.01)
(Continued)

(52) U.S. Cl.
CPC ............. *B29C 48/92* (2019.02); *B29C 48/022* (2019.02); *G01N 27/02* (2013.01); *G01N 27/041* (2013.01);
(Continued)

(58) Field of Classification Search
CPC .......... B29C 2948/92047; B29C 2948/92219; B29C 2948/92428; B29C 35/0288;
(Continued)

(56) References Cited

U.S. PATENT DOCUMENTS 8,217,669 B1 *   7/2012   Watkins, Jr. ........... G01N 27/12
                                                         324/693
2002/0135385 A1   9/2002  Magill
(Continued)

FOREIGN PATENT DOCUMENTS

| EP | 2 500 718 A2 | 9/2012 |
| EP | 3672067 A1 | 6/2020 |
| JP | H02 275349 A | 10/1990 |

OTHER PUBLICATIONS

International Search Report and Written Opinion of International Application No. PCT/IB2020/057508, mailed Nov. 2, 2020, 27 pages.

(Continued)

*Primary Examiner* — Amy He
(74) *Attorney, Agent, or Firm* — Heslin Rothenberg Farley and Mesiti, PC; Victor A. Cardona Esq.

(57) ABSTRACT

A method for measuring a degree of cross-linking of a component of elastomeric material obtained as a result of a hot-forming process, includes a preliminary calibration step in which a plurality of samples are provided, made of the same material as the component. The samples have different degrees of cross-linking following respective hot-forming processes conducted for different periods of time. The (Continued)

Figure 2:
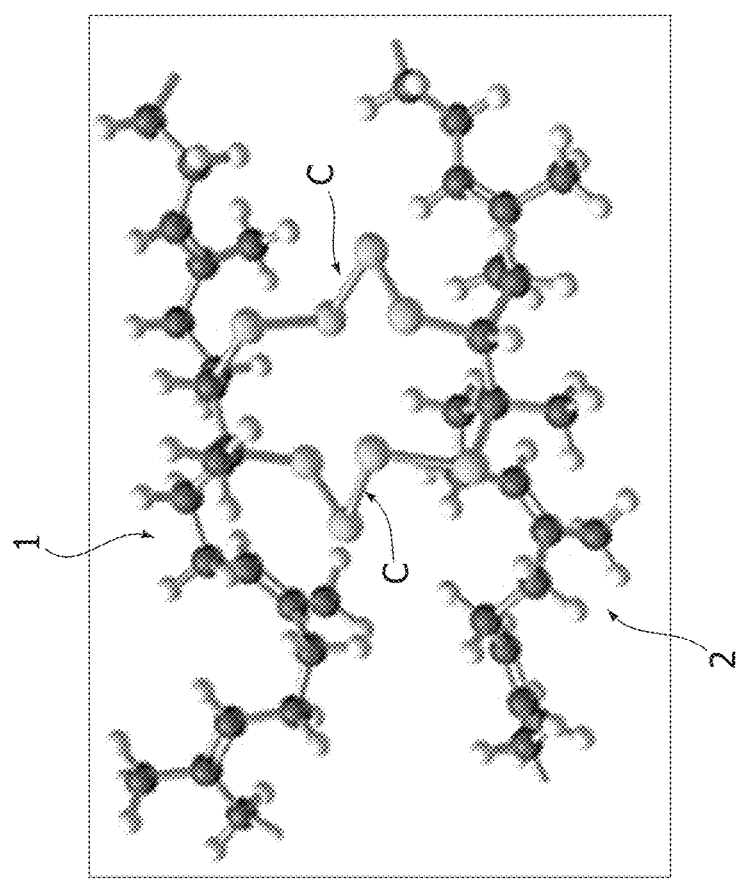

preliminary calibration step includes providing a measuring device having an electrical circuit, in which a voltage generator is arranged in series with metal contacts configured to selectively receive a sample, and an ammeter, positioning a sample between said metal contacts, providing a predetermined voltage value, and detecting the corresponding current value by means of said ammeter. The aforesaid steps are repeated for each sample so as to obtain a calibration map that associates a given degree of cross-linking of the material constituting said component with each determined value of electrical conductivity.

3 Claims, 5 Drawing Sheets

(51) Int. Cl.
  *B29K 21/00* (2006.01)
  *G01N 27/02* (2006.01)
  *G01N 27/04* (2006.01)
  *B29K 105/24* (2006.01)
(52) U.S. Cl.
  CPC .......... *B29C 2948/92047* (2019.02); *B29C 2948/92219* (2019.02); *B29C 2948/92428* (2019.02); *B29K 2021/006* (2013.01); *B29K 2105/24* (2013.01); *B29K 2995/0005* (2013.01)
(58) Field of Classification Search
  CPC .......... B29C 48/022; B29C 48/92; B29D 2030/0066; B29D 30/0061; B29K 2021/006; B29K 2105/24; B29K 2995/0005; G01N 27/041; G01N 33/44; G01N 27/02; G01N 27/04
  See application file for complete search history.

(56) References Cited

U.S. PATENT DOCUMENTS

2002/0166372 A1    11/2002  Farne
2005/0119785 A1*   6/2005  Magill .............. B29C 35/0288
                                              700/199

OTHER PUBLICATIONS

First Office Action dated Mar. 3, 2025, from related Chinese Patent Application No. 202080040530.2 filed Aug. 10, 2020, entitled "A Method of Measuring the Cross-Linking Degree of a Component of Elastomeric Material", 15 pp.

* cited by examiner

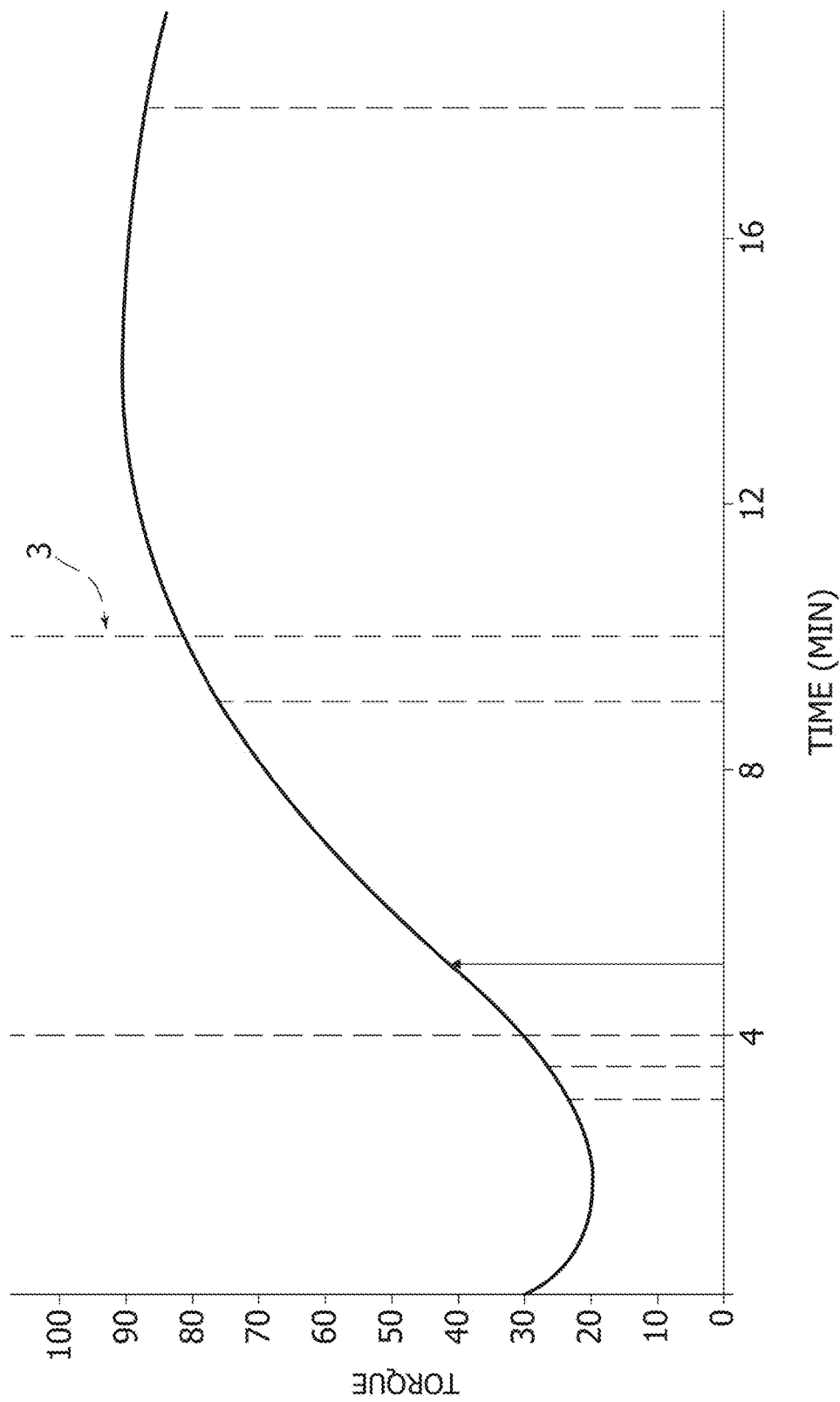

METHOD FOR USE IN MEASURING A PROPERTY OF AN AUTOMOBILE COMPONENT

CROSS REFERENCE TO RELATED APPLICATIONS

This application is a national stage filing under section 371 of International Application No. PCT/IB2020/057508, filed on Aug. 10, 2020, published in English on Jun. 17, 2021 as WO 2021/116784 and which claims priority to European Patent Application No. 19214709.8 filed on Dec. 10, 2019, the entire disclosure of these applications being hereby incorporated herein by reference.

FIELD OF THE INVENTION

The present invention relates to a method for measuring the cross-linking degree of a finished component of at least partially electrically-conductive elastomeric material, configured for being installed on-board of a motor-vehicle.

The present invention also relates to a quality control apparatus and a correspondent method for controlling the quality of a finished component of at least partially electrically-conductive elastomeric material, configured for being installed on-board of a motor-vehicle.

The present invention is applied to finished components of elastomeric material obtained by a hot-forming process, intended to be mounted on-board a motor-vehicle.

PRIOR ART

The expression "cross-linking of an elastomeric material" means a process by which the polymeric chains of the material undergo a reaction which creates chemical bonds between different chains. With the formation of these bonds, the physical properties of the material vary according to the quantity and type of these bonds. The cross-linking process of rubber is commonly called the vulcanization process.

Methods for measuring the cross-linking state of an elastomeric material have already been proposed in the past, of the type in which the measurement is carried out by means of systems configured to correlate the cross-linking state with the mechanical properties of the material (for example hardness, load and elongation at break, "compression set"). These known methods can have some disadvantages, such as high implementation times and costs, and margins of uncertainty on the results obtained.

Moreover, in some cases, measuring the degree of cross-linking of the components may be unfeasible by the known methods, since the dimensions of these components are incompatible with the dimensions required to carry out the measurement by means of mechanical tests such as, for example, the load and elongation at break.

To date, elastomeric materials are the basis for producing various components present on board motor-vehicles, for example, tubular components, gaskets, suspension components, tires, etc.

In view of the above, there is a particular need to measure the degree of cross-linking of the materials constituting these components, in order to be able to carry out an in-depth analysis and identify possible problems in their production process, so as to avoid the use of defective components that could cause malfunctions during operation.

The present invention is based on the need to propose a method for measuring the degree of cross-linking of a component made of elastomeric material, which is reliable and simple to implement.

OBJECT OF THE INVENTION

The object underlying the present invention is to provide a method of the type indicated at the beginning of the present description, and a relative apparatus, which overcomes the aforementioned drawbacks of the prior art, so as to provide a repeatable method, which leads to reliable results, and adaptable to elastomeric components with different compositions and sizes.

A further object of the invention is that of achieving the aforesaid objective with a simple method to implement that is inexpensive.

SUMMARY OF THE INVENTION

In order to achieve the aforesaid objects, the invention relates to a method for measuring the cross-linking degree of a finished component of at least partially electrically-conductive elastomeric material, configured for being installed on-board of a motor-vehicle, said method comprising the following steps:
performing a hot-forming process for obtaining a finished component of at least partially electrically-conductive elastomeric material, said component being in its final configuration for being installed on-board of a motor-vehicle,
performing a preliminary calibration step comprising:
providing a plurality of samples made of the same material of said component, wherein said samples are obtained with different degrees of cross-linking following respective hot-forming processes conducted for different periods of time;
leaving said samples in a resting condition at room temperature;
providing a measuring device comprising an electrical circuit, in which a voltage generator is arranged in series with metal contacts (7) configured to selectively receive a sample (8), and an ammeter (6);
positioning a sample (8) between said metal contacts, so that said sample is not subject to bending,
providing a predetermined voltage value by means of said voltage generator;
detecting the corresponding current value by means of said ammeter;
leaving the sample again in a resting configuration at room temperature;
repeating the aforesaid steps of positioning the sample between the metal contacts, providing a voltage value and detecting the corresponding current value, in which the voltage value generated by said voltage generator is different with respect to the previously applied voltage value;
repeating the aforementioned steps for each sample, so as to obtain a calibration map that associates a given degree of cross-linking of the material constituting said component with each determined value of electrical conductivity;
performing a step of measuring the electrical conductivity of said component in its final configuration for being installed on-board of a motor-vehicle, to compare said conductivity value with a predetermined threshold value obtained from said calibration map and obtaining information on the quality of the component based on the aforesaid comparison;

in such a way that, after obtaining information on the quality of the component based on the aforesaid comparison, if the quality of the component is lower than a minimum acceptable value, proceeding to scrap the component obtained with a hot forming process carried out with incorrect conditions, thus avoiding installation of a defected component on board a motor vehicle.

Preferably, during said preliminary calibration step, for each voltage value applied on each sample, measuring the corresponding current value by means of said ammeter is performed consecutively at least three times, so as to have a statistical evaluation of the phenomenon.

Preferably, said predetermined voltage value is between 1 V and 20 V, and is provided by said voltage generator for at least (60±1) seconds.

Preferably, the step of leaving the sample again in the resting configuration at room temperature following the measurement of the current value is continued for a time of at least (300±1) seconds.

The present invention also relates to a quality control apparatus for controlling the quality of a component made of at least partially electrically-conductive elastomeric material, obtained by a hot-forming process and being in its final shape configured for being installed on-board of a motor-vehicle, said quality control apparatus being configured for evaluating the cross-linking degree of the component, said quality control apparatus comprising:

an electrical circuit configured to measure the electrical conductivity of the component, and an electronic controller associated with a memory containing a calibration map that associates a given degree of cross-linking of the material constituting said component with each determined value of electrical conductivity, said electronic controller being programmed to receive information on the electrical conductivity value of the component from said electronic circuit, to compare said conductivity value with a predetermined threshold value obtained by said calibration map and to provide information on the quality of the component on the basis of the aforesaid comparison.

Further characteristics and advantages of the invention will become apparent from the following description, provided purely by way of non-limiting example, with reference to a preferred embodiment of the invention.

DETAILED DESCRIPTION OF THE EMBODIMENTS

Figure 1:
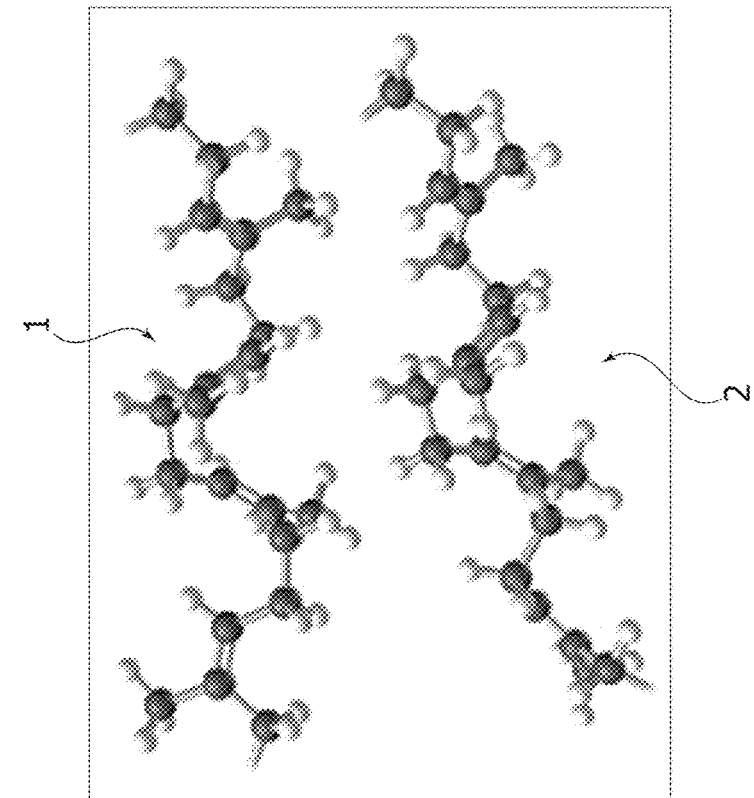
Figure 5:
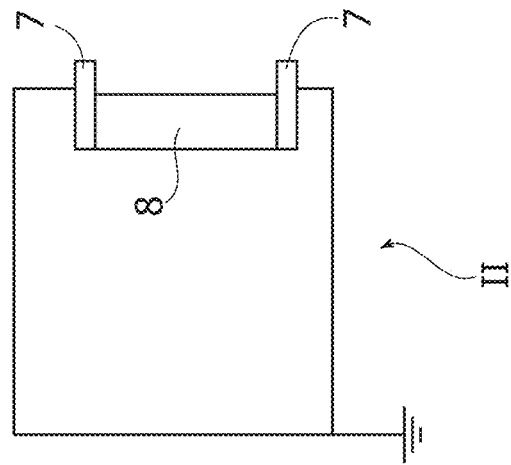
Figure 4:
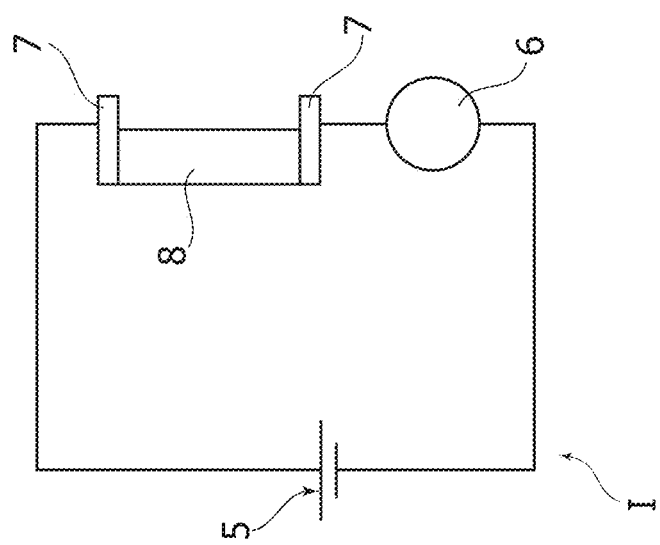
Figure 6:
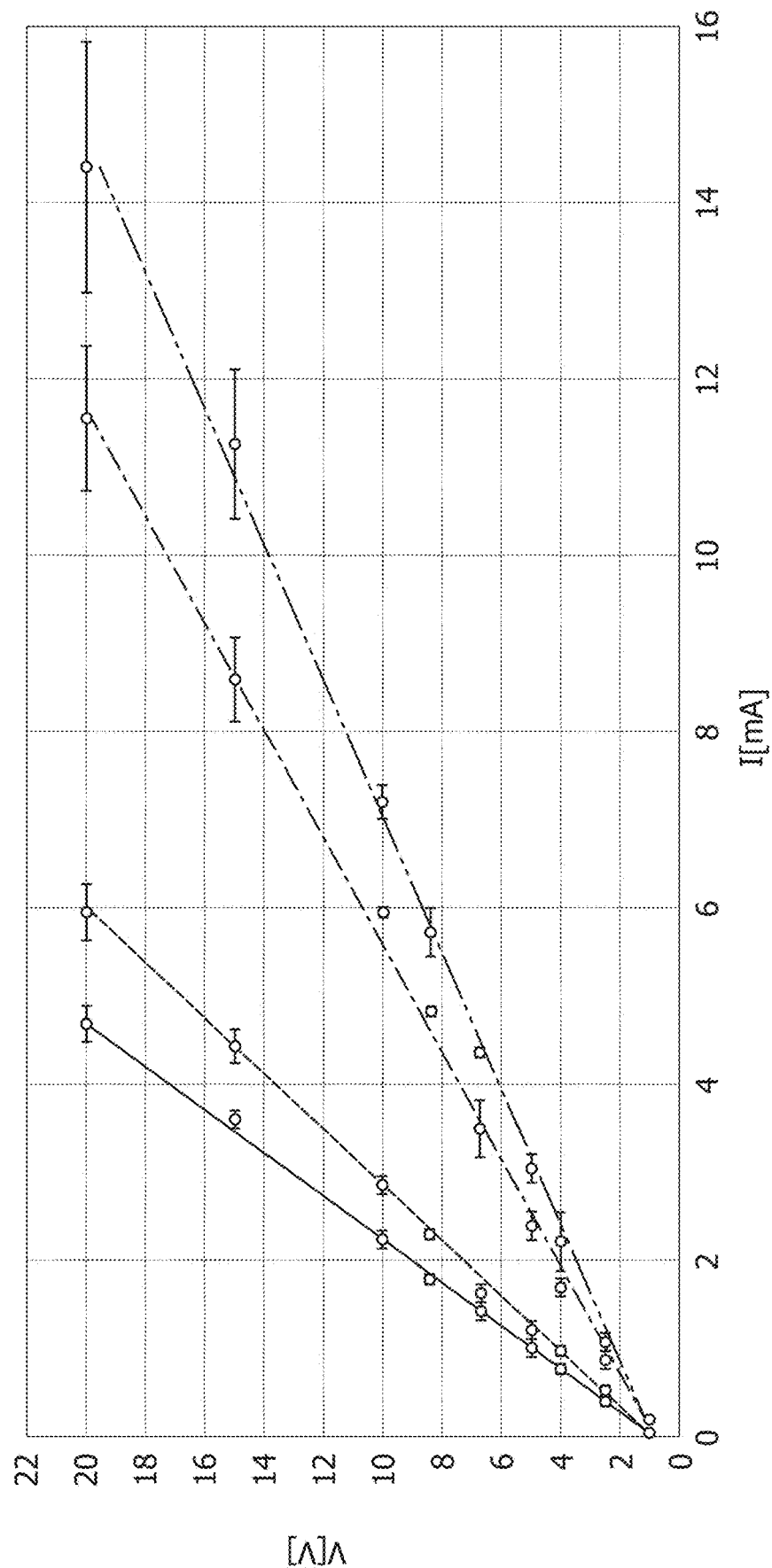
Figure 7:
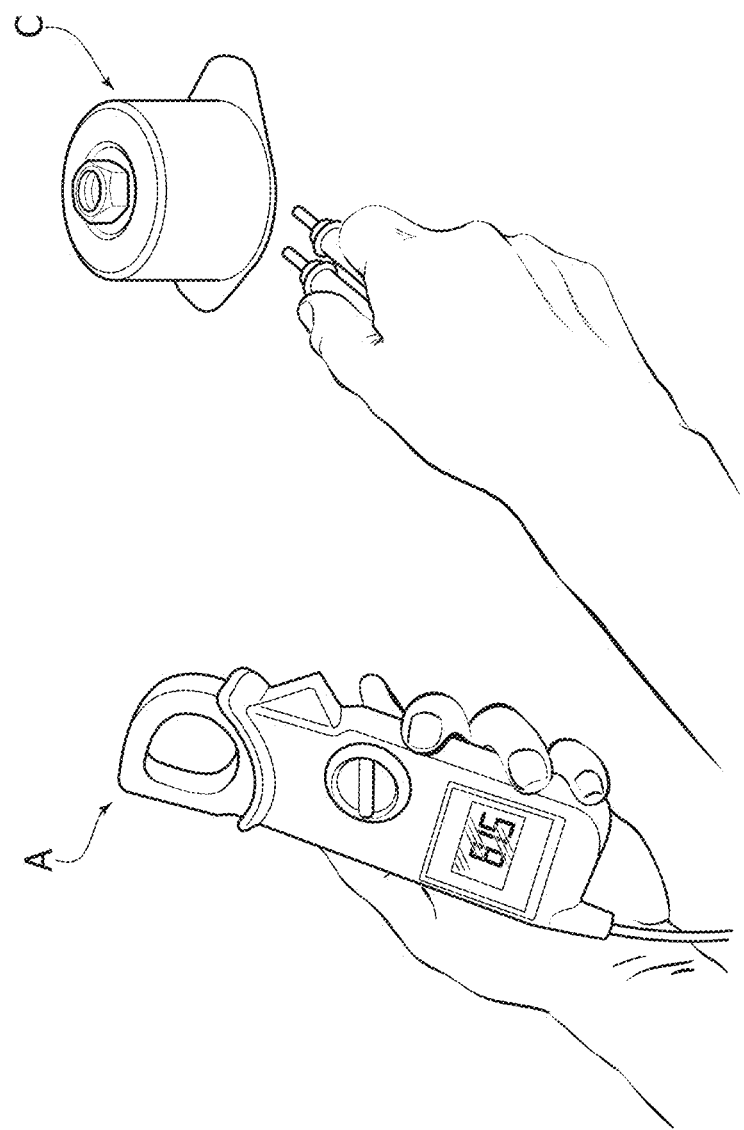

Embodiments of the invention are illustrated in the attached drawings, wherein:

FIGS. 1 and 2 illustrate schematic views of chemical bonds between the polymeric chains of an elastomeric material, before and after a vulcanization process, respectively, FIG. 3 is a graph indicating the correlation between the degree of cross-linking of an elastomeric material and the forming process to which it is subjected, FIGS. 4 and 5 are schematic views that illustrate some steps of the method according to the invention, FIG. 6 is a calibration map obtained following a step of the method according to the invention, and FIG. 7 illustrates a schematic perspective view of a measuring apparatus.

In the following description, various specific details are illustrated aimed at a thorough understanding of examples of one or more embodiments. The embodiments can be implemented without one or more of the specific details, or with other methods, components, materials, etc. In other cases, known structures, materials, or operations are not shown or described in detail to avoid obscuring various aspects of the embodiments.

The reference to "an embodiment" in the context of this description indicates that a particular configuration, structure or characteristic described in relation to the embodiment is included in at least one embodiment. Therefore, phrases such as "in an embodiment", possibly present in different places of this description do not necessarily refer to the same embodiment. Moreover, particular conformations, structures or characteristics can be combined in a suitable manner in one or more embodiments and/or associated with the embodiments in a different way from that illustrated here, for example, a characteristic here exemplified in relation to a figure may be applied to one or more embodiments exemplified in a different figure.

The references illustrated here are only for convenience and do not, therefore, delimit the field of protection or the scope of the embodiments.

FIGS. 1 and 2 are schematic views showing some polymeric chains 1, 2 of a component made of an elastomeric material. In FIG. 1, the chains 1, 2 are illustrated in a state in which the rubber vulcanization method has not yet taken place. According to a technique known per se, vulcanization creates a modification of the molecular conformation of the polymer, causing an increase in elasticity and tensile strength, and the suppression of negative properties such as abrasiveness. Typically, vulcanization is carried out using the elastomer in question, a source of sulfur and various additives; the combination of these products constitutes the compound. Pressure and temperature conditions may vary depending on the specific process involved.

Following this process, the polymeric chains 1, 2 undergo a reaction that creates chemical bonds C between the different chains 1, 2 (FIG. 2). By forming these bonds C, the physical properties of the component vary according to the relative quantity of these bonds.

FIG. 3 illustrates an example of a rheometric curve of an elastomeric material that indicates the progress of the cross-linking state of the material during its hot-forming process. In this figure, the time of the forming process is indicated on the horizontal axis, and an operational parameter of a measuring instrument (rheometer) is indicated on the vertical axis. From the curve it is possible to identify the value of t90 (indicated with the reference 3), which indicates the time of the forming process in which 90% of the cross-linking process has occurred. Typically, in a hot-forming method of an elastomeric material, in particular in the extrusion or molding process, when the time of the forming method reaches the value of t90, the component is removed from the mold and allowed to cool to complete the cross-linking process, until the component is completely cooled.

According to the illustrated example, the method according to the invention, aimed at measuring the cross-linking degree of a component of elastomeric material, comprises a preliminary calibration step. In order to make the method feasible, the elastomeric material must be at least partially electrically-conductive. For this reason, the elastomers used in the method of the invention must contain black carbon particles.

The preliminary calibration step comprises providing a plurality of samples 8 of the same material as component C of which the cross-linking degree is to be measured. The samples 8 have identical dimensions (thickness, width and length). Taking as reference the rheometric curve of the material on which the measurement is to be carried out, the aforesaid samples 8 are obtained with different degrees of cross-linking following respective hot-forming processes conducted for different periods of time.

Preferably, the samples 8 are plate-shaped and are obtained following a process of extrusion or hot molding. Of course, the plate shape is to be considered purely by way of example, since the samples can be made with other shapes and sizes suitable for achieving the preset purposes (for example, of tubular shape).

In various embodiments, as in the one illustrated, the preliminary calibration comprises providing a measuring device comprising an electrical circuit I in which a voltage generator 5 is arranged, along with metal contacts 7 configured to selectively receive one of the samples, and an ammeter 6. Preferably, these components are arranged in series with each other.

The measuring device is provided out of a mold in which the component C is obtained by a hot-forming process.

Following a step in which the samples 8 are left in a resting condition at room temperature, after their hot-forming, one of the samples 8 is positioned between the metal contacts 7. The sample 8 must be positioned so it is not subject to stresses, for example, bending.

In a concrete embodiment, the metal contacts 7 are made of copper and have a hood-like shape to receive the ends of the plate-shaped sample 8.

In various embodiments, as in the illustrated one, the calibration step further comprises the following steps:
  providing a predetermined voltage value by means of the voltage generator 5;
  detecting the corresponding current value by means of the ammeter 6, corresponding to the conductivity value of the sample 8,
  leaving the sample 8 again in a resting configuration at room temperature,
  repeating the steps of positioning the sample between the metal contacts 7, providing a voltage value and detecting the corresponding current value, in which the voltage value generated by the voltage generator 5 is different with respect to the previously applied voltage value.

Preferably, for each voltage value applied, the measurement of the corresponding current value by means of the ammeter 6 is performed consecutively at least three times, so as to have a statistical evaluation of the phenomenon.

Still according to a further preferred characteristic of the invention, the predetermined voltage value applied is comprised between 1 V and 20 V, and is supplied by the generator 5 for a time of at least (60±1) seconds.

Still according to a preferred characteristic of the invention, the step of leaving the sample again in the resting configuration at room temperature following the measurement of the current value is continued for a time of at least (300±1) seconds.

As illustrated in FIG. 5, the samples 8 can be left in the resting condition by positioning them on the metal contacts 7 arranged in the electrical circuit II.

By repeating the aforesaid preliminary calibration steps for each sample 8, it is possible to obtain a calibration map M, illustrated in FIG. 6, which associates a given cross-linking degree of the material of which each sample 8 is made with each determined value of electrical conductivity. The example illustrated in FIG. 6 includes three straight lines 8A, 8B and 8C, identifying different measurements made on three different samples 8 of the same material, obtained with different degrees of cross-linking interrupting the molding process at different times, respectively $t1<t2<t3$.

More specifically, the calibration map of FIG. 6 shows the voltage value supplied by the voltage generator on the y-axis, and the corresponding determined electrical conductivity value on the x-axis. The line 8A identifying the sample with a lower cross-linking degree corresponding to the lower forming time t1 has lower electrical conductivity values than the samples identified with the straight lines 8B and 8C.

According to the method according to the invention, following the preliminary calibration step indicated above, which leads to defining of the calibration map M for a specific type of elastomeric material (for example, illustrated in FIG. 6), the method includes a measuring step carried out directly on the component C of elastomeric material, whose degree of cross-linking is to be verified. This step of the method envisages measuring the electrical conductivity of the component C made of the same material as the samples 8, of which information must be obtained concerning the quality of its forming method.

The measurement is carried out following the application of different voltage values, so as to obtain a straight line R on the calibration map M identifying the electrical conductivity of the component C.

The method according to the invention therefore comprises a step of comparing the conductivity value of the samples 8 and of the component C, to obtain information on the quality of the component C on the basis of the aforesaid comparison.

In the example shown in FIG. 6, assuming that the straight line 8C identifies the acceptability margin, the identifying straight line R of the electrical conductivity of the real component C, provides information on the cross-linking degree of the component C. In this case, the quality of the forming process of the component C is lower than a minimum acceptable value. Consequently, again with reference to the specific case of the drawings, it is possible to proceed with the discarding of component C, since it was produced with a forming method carried out in incorrect conditions (linked, for example, to incorrect temperature, pressure or duration values of the process), thus avoiding installation of a defective component on the vehicle.

As already indicated, the invention is also directed to an apparatus A (schematically illustrated in FIG. 7), for quality control of a component C of elastomeric material obtained by a hot-forming process, comprising:
  an electrical circuit to measure the electrical conductivity of the component C, and
  an electronic controller associated with a memory containing a calibration map that associates a given degree of cross-linking of the material constituting component C with each determined electrical conductivity value. The electronic controller is programmed to receive information on the value of electrical conductivity of the component C from the electronic circuit, to compare said conductivity value with a predetermined threshold value, and provide information on the quality of the component based on the aforesaid comparison. In this way, it is possible to obtain information on the quality of the production method of the component C, thus avoiding the mounting of a component on motor-vehicles that does not comply with the required requirements, which could lead to malfunctions during operation.

As shown in FIG. 7, the component C can be a motor-vehicle elastic bushing or a motor-vehicle elastic dowel.

The electronic controller is configured for providing a warning signal if, following the aforesaid comparison, the quality of the component forming process results lower with respect to a minimum acceptable value, so as to proceed with scrapping the component, since obtained with a hot-forming process carried out with incorrect conditions, thus avoiding the installation on-board of a motor-vehicle with a defected component.

The apparatus A is a portable electronic device, so as to provide high flexibility during the use.

The apparatus A can comprise a monitor for visualizing said warning signal. The apparatus A can be configured for emitting an acoustic warning signal. The apparatus A is connectable to another electronic elaborator.

Thanks to the characteristics indicated above, the method and the relative apparatus allow a series of important advantages to be achieved. First of all, the measuring method is repeatable and reliable. Secondly, the method according to the invention is adaptable to elastomeric components with different compositions and sizes. Moreover, the method according to the invention is simple to implement and inexpensive.

Of course, without prejudice to the principle of the invention, the details of construction and the embodiments may vary widely with respect to those described and illustrated purely by way of example, without departing from the scope of the present invention.

The invention claimed is:

1. A method for measuring a cross-linking degree of a finished component made of at least partially electrically-conductive elastomeric material, configured for being installed on-board of a motor-vehicle,
   said method comprising the following steps:
   performing a hot-forming process for obtaining a finished component of at least partially electrically-conductive elastomeric material,
   performing a preliminary calibration step comprising:
   providing a plurality of samples made of a same material as said component, wherein said samples are obtained with different degrees of cross-linking following respective hot-forming processes conducted for different periods of time;
   said samples are homogeneous in terms of size and production process;
   said samples are shaped like a plate;
   leaving said samples in a resting condition at room temperature for a time of at least 24 hours;
   providing a measuring device comprising an electrical circuit, in which a voltage generator is arranged in series with metal contacts configured to selectively receive a sample of said samples, and an ammeter;
   positioning a first sample of said samples between said metal contacts, so that said first sample is not subject to bending,
   providing a predetermined voltage value by means of said voltage generator to said first sample;
   said predetermined voltage value is between 1 V and 20V, and is provided by said voltage generator for at least 60±1 seconds;
   detecting a corresponding current value of said first sample by means of said ammeter;
   leaving the first sample again in the resting configuration at room temperature for a time of at least 300±1 seconds;
   repeating the aforesaid steps of positioning the first sample between the metal contacts, providing a second voltage value and detecting a second corresponding current value, in which the second voltage value generated by said voltage generator is different with respect to the previously applied voltage value;
   repeating the aforementioned steps for each sample of the plurality of samples, so as to obtain a calibration map of sar activity values that associates a given degree of cross-linking of the material constituting said component with a determined value of electrical conductivity based on the predetermined voltage;
   determining a threshold value based on the calibration map of sample conductivity values;
   performing a step of measuring a component electrical conductivity of said component and comparing said component conductivity of said component with the threshold value to determine if said component is defective and
   scrapping said component based on the comparing said component conductivity of said component with the threshold value to avoid installation of said component on the motor vehicle when said component is defective.

2. A method according to claim 1, wherein during said preliminary calibration step, for each voltage value applied on each sample, the detecting the corresponding current value by means of said ammeter is performed consecutively at least three times, so as to have a statistical evaluation of the phenomenon.

3. A method according to claim 1 wherein said hot-forming processes include an extrusion or molding process.

* * * * *